(12) United States Patent
Chu et al.

(10) Patent No.: US 10,712,257 B2
(45) Date of Patent: Jul. 14, 2020

(54) INSPECTION DEVICE AND INSPECTION CAGE UNIT THEREOF

(71) Applicant: Wistron Corp., New Taipei (TW)

(72) Inventors: Yu-Jung Chu, New Taipei (TW); Chen An Sung, New Taipei (TW)

(73) Assignee: WISTRON CORP., New Taipei (TW)

( * ) Notice: Subject to any disclaimer, the term of this patent is extended or adjusted under 35 U.S.C. 154(b) by 0 days.

(21) Appl. No.: 16/201,963

(22) Filed: Nov. 27, 2018

(65) Prior Publication Data

US 2020/0033254 A1   Jan. 30, 2020

(30) Foreign Application Priority Data

Jul. 26, 2018   (TW) .............................. 107125875 A

(51) Int. Cl.
*G01N 21/03* (2006.01)
*H04N 5/225* (2006.01)
*G01N 33/483* (2006.01)

(52) U.S. Cl.
CPC ..... *G01N 21/0303* (2013.01); *G01N 33/4833* (2013.01); *H04N 5/2258* (2013.01); *G01N 2021/0342* (2013.01)

(58) Field of Classification Search
CPC ........... G01N 21/0303; G01N 33/4833; H04N 5/2258
See application file for complete search history.

(56) References Cited

U.S. PATENT DOCUMENTS

2015/0008339 A1*  1/2015  French ............... G01N 21/4795
                                                  250/458.1
2015/0168706 A1*  6/2015  Schweinitzer ....... G02B 21/367
                                                       348/80

FOREIGN PATENT DOCUMENTS

CN         201340395 Y      11/2009

* cited by examiner

*Primary Examiner* — Girumsew Wendmagegn

(57) ABSTRACT

An inspection device is provided. The inspection device includes a platform, a cage, a holder and an image capturing module. The cage is disposed on the platform, wherein the cage includes a first transparent side and a second transparent side, and the first transparent side and the second transparent side are not coplanar. The holder is disposed in the cage. The image capturing module captures a first image from the first transparent side, and it captures a second image from the second transparent side.

18 Claims, 11 Drawing Sheets

INSPECTION DEVICE AND INSPECTION CAGE UNIT THEREOF

CROSS REFERENCE TO RELATED APPLICATIONS

This Application claims priority of Taiwan Patent Application No. 107125875, filed on Jul. 26, 2018, the entirety of which is incorporated by reference herein.

BACKGROUND OF THE INVENTION

Field of the Invention

The present invention relates to an inspection device, and in particular to an inspection device that captures images of an object.

Description of the Related Art

A conventional biological tissue inspection module includes a transparent box and a housing. First, biological tissue is placed into the transparent box. Then, the transparent box is inserted into the housing. The housing presses against the biological tissue, and the biological tissue is thereby sufficiently attached to the bottom of the transparent box. Next, glycerin is injected into the transparent box via an injection hole in the housing. Then, the biological tissue inspection module is placed into an analyzer. The analyzer captures an image from the bottom of the transparent box, and the image is analyzed. Conventionally, only one image of one side of the biological tissue can be captured for inspection, and inspection efficiency is low.

BRIEF SUMMARY OF THE INVENTION

In one embodiment, an inspection device is provided. The inspection device includes a platform, a cage, a holder and an image capturing module. The cage is disposed on the platform, wherein the cage comprises a first transparent side and a second transparent side, and the first transparent side and the second transparent side are not coplanar. The holder is disposed in the cage. The image capturing module captures a first image from the first transparent side, and it captures a second image from the second transparent side.

In one embodiment, the image capturing module comprises a first image capturing element and a second image capturing element, the first image capturing element corresponds to the first transparent side and captures the first image from the first transparent side, and the second image capturing element corresponds to the second transparent side and captures the second image from the second transparent side.

In one embodiment, the first transparent side is perpendicular to the second transparent side, the second transparent side contacts the platform, the platform comprises a stage transparent portion, the second transparent side corresponds to the stage transparent portion, the second image capturing element corresponds to the stage transparent portion and captures the second image from the second transparent side.

In one embodiment, the image capturing module comprises a first image capturing element. The cage is rotated relative to the first image capturing element. The first image capturing element captures the first image from the first transparent side. The first image capturing element captures the second image from the second transparent side.

In one embodiment, the platform comprises a rotational plate, an actuator and a transmission unit. The actuator is connected to the transmission unit. The transmission unit is connected to the rotational plate. The actuator moves the transmission unit. The transmission unit rotates the rotational plate. The stage transparent portion is formed on the rotational plate.

In one embodiment, the actuator comprises a motor, and the transmission unit comprises a pulley and a belt. The pulley is connected to the motor, and the belt connects the pulley to the rotational plate.

In one embodiment, the actuator comprises a motor, and the transmission unit comprises a gear. The gear is connected to the motor, and the gear rotates the rotational plate. The stage transparent portion is formed on the rotational plate.

In another embodiment, an inspection cage unit is provided. The inspection cage unit includes a cage and a holder. The cage comprises a first transparent side and a second transparent side, wherein the first transparent side and the second transparent side are not coplanar. The holder is disposed in the cage. The cage comprises a cage body and a cage cover. The cage body comprises the first transparent side and the second transparent side. The holder is disposed in the cage body. The cage cover covers the holder and seals the cage body.

In one embodiment, the whole cage body is made of a transparent material.

In one embodiment, the cage body comprises a first transparent plate and a second transparent plate, the first transparent plate and the second transparent plate are embedded to surfaces of the cage body. The first transparent side is formed on the first transparent plate. The second transparent side is formed on the second transparent plate.

In one embodiment, the cage cover comprises an O-ring, and when the cage cover seals the cage body, the O-ring abuts an inner wall of the cage body.

In one embodiment, the cage cover comprises an abutting portion, and when the cage cover seals the cage body, the abutting portion abuts the holder.

In one embodiment, the holder comprises a base and a plurality of cantilever arms, the cantilever arms are connected to the base, and when the cage cover seals the cage body, the cage cover abuts the base.

In one embodiment, each cantilever arm comprises a first end, a second end and a pressing portion. The pressing portion is located between the first end and the second end. The first end is connected to the base, and the second end is a free end.

In one embodiment, each pressing portion is sheet-shaped, and the width of the pressing portion is greater than the width of each of the other portions of the cantilever arm.

In one embodiment, the cage body comprises a plurality of corners, and when the holder is in the cage body, the cantilever arms respectively abut the corners.

In one embodiment, the base comprises at least one bending portion, and the bending portion is located between the two adjacent cantilever arms.

In one embodiment, the base further comprises a wedging hole, and an injector is adapted to be connected to the wedging hole.

In one embodiment of the invention, the object can be biological tissue. The image capturing module captures five images of the object. Therefore, the object (biological tissue) can be sufficiently inspected, and the inspection time is reduced.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
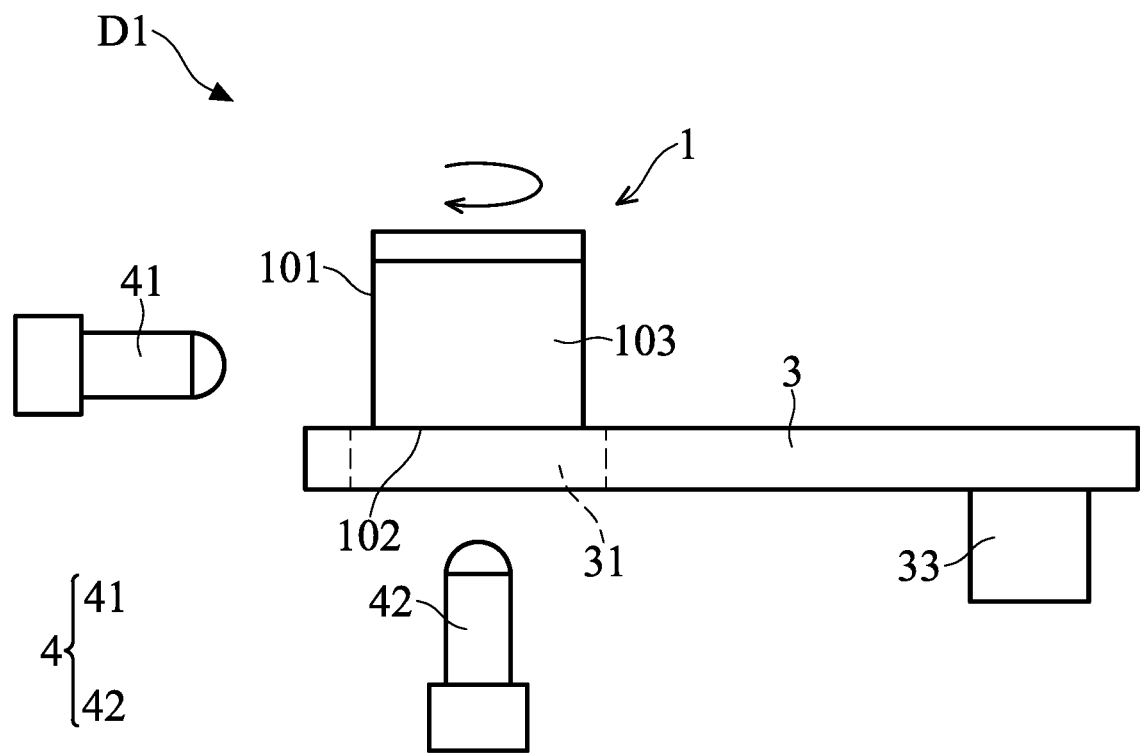
FIG. 1 shows an inspection device of an embodiment of the invention.

FIG. 1 shows an inspection device D1 of an embodiment of the invention. The inspection device D1 is adapted to inspect an object T. The inspection device D1 includes a platform 3, a cage 1, a holder 2 (with reference to FIG. 2A) and an image capturing module 4. In FIG. 1, the object T is not shown, which is located in the cage 1. In the embodiments of the invention, the object T can be biological tissue. The cage 1 is disposed on the platform 3. In one embodiment of the invention, the image capturing module 4 captures five images of the object T (biological tissue). Therefore, the object T (biological tissue) can be sufficiently inspected, and the inspection time is reduced.

Figure 2A:
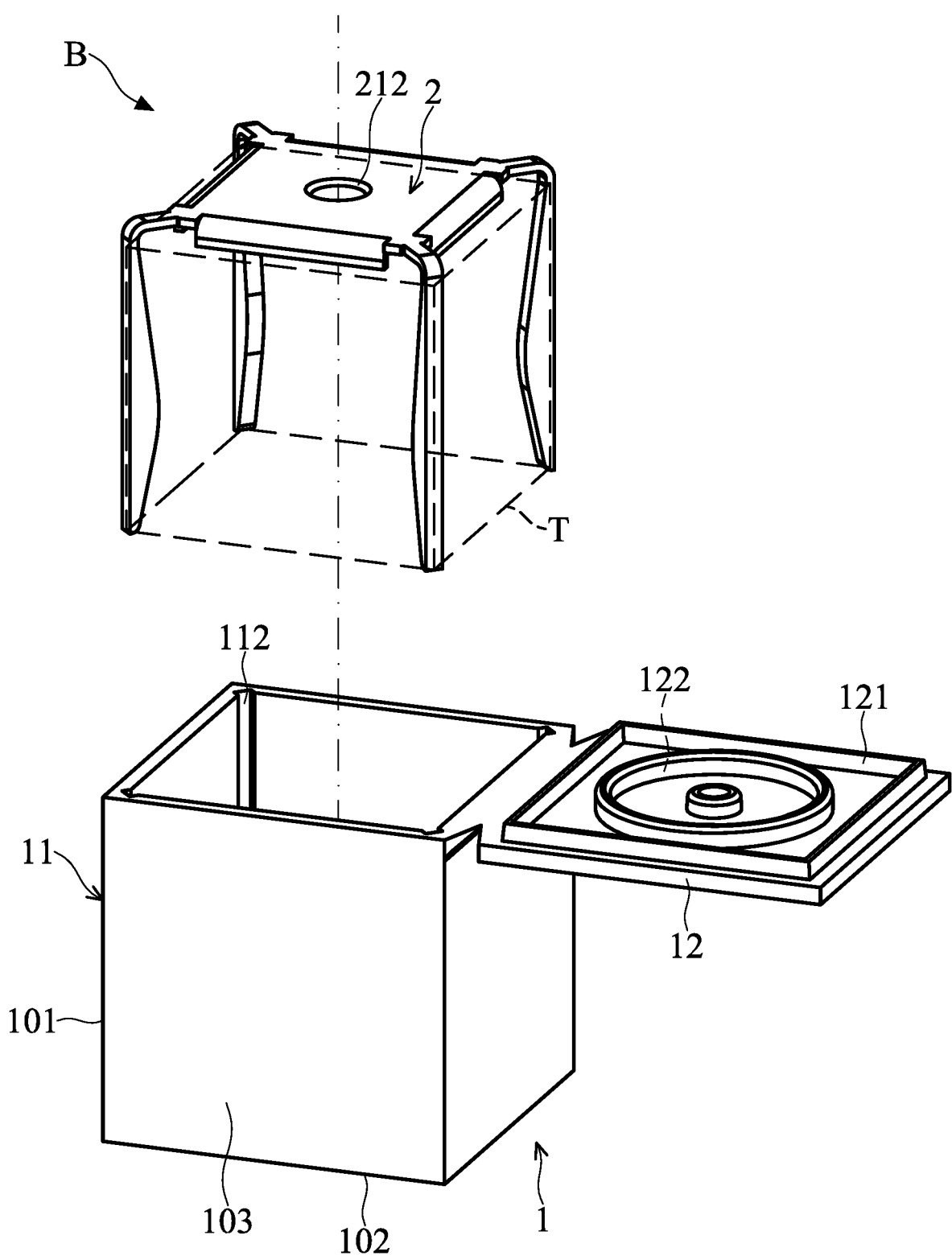
FIG. 2A shows an inspection cage unit of an embodiment of the invention.
Figure 2B:
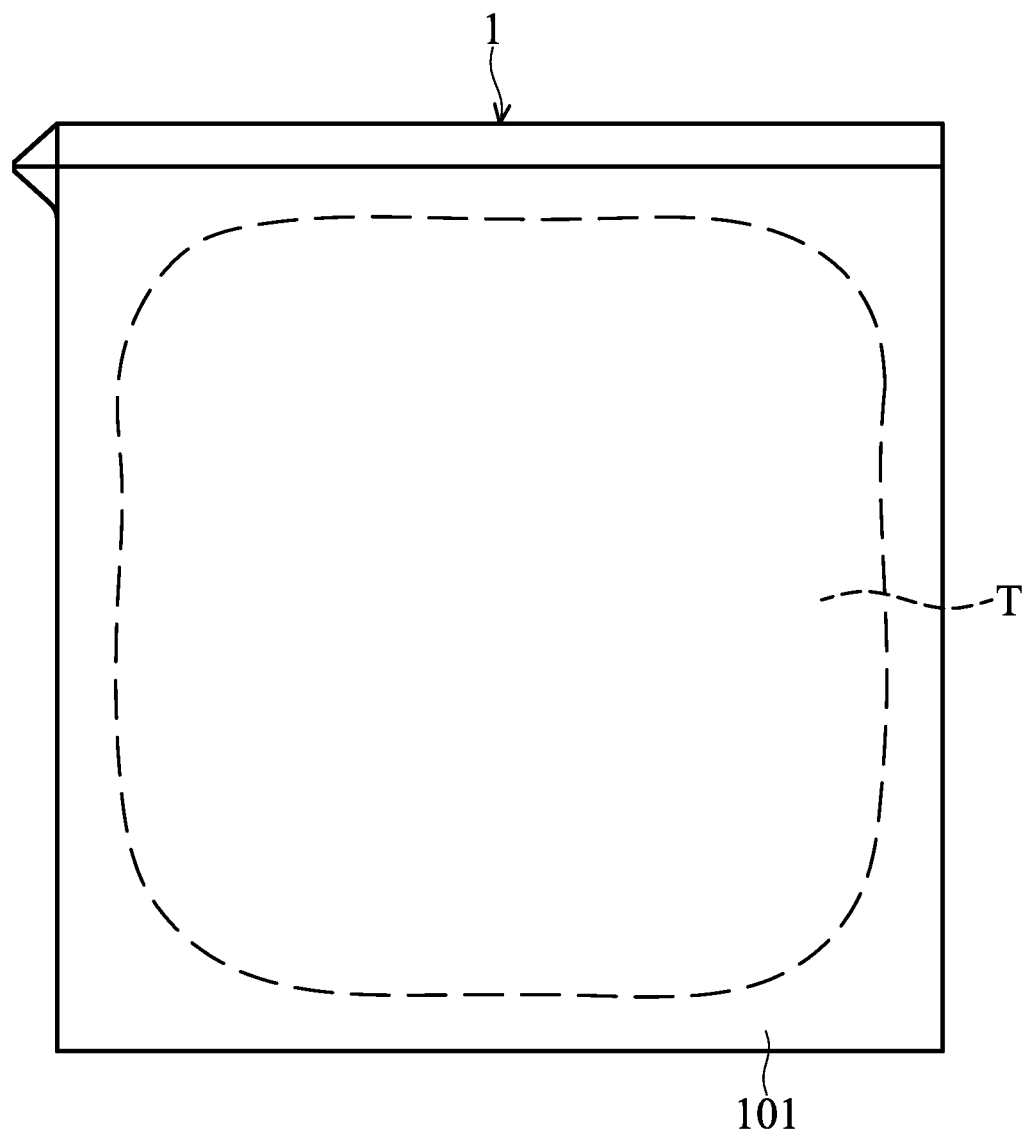
FIG. 2B shows an object attached to at least a portion of a transparent side of a cage of an embodiment of the invention.

FIG. 2A shows an inspection cage unit B of an embodiment of the invention. The inspection cage unit B includes a cage 1 and a holder 2. The cage 1 comprises a plurality of transparent sides (including a transparent side 101, a transparent side 102, a transparent side 103, etc.). The holder 2 holds the object T. In one embodiment, the object T is cut according to the size and the shape of the holder 2 to be held by the holder 2 (in this embodiment, the object is cubic shaped). The holder 2 and the object T are disposed in the cage 1. The object T is attached to at least a portion of each transparent side (for example, it is attached to at least a portion of transparent side 101, a portion of transparent side 102, and a portion of transparent side 103). FIG. 2B shows the object T attached to at least a portion of the transparent side 101. With reference to FIG. 1, the image capturing module 4 captures images from the transparent sides.

With reference to FIG. 2A, in the embodiments above, transparent side 101, transparent side 102 and transparent side 103 are not coplanar. The cage 1 comprises a cage body 11 and a cage cover 12. The cage body 11 comprises the transparent side 101, the transparent side 102 and the transparent side 103. The holder 2 and the object T are disposed in the cage body 11. The cage cover 12 covers the holder 2 and the object T, and seals the cage body 11.

In one embodiment, the whole cage body 11 is made of transparent materials, such as acrylic or other transparent materials. In this embodiment, the cage 1 is a hexagonal cube. However, the disclosure is not meant to restrict the invention. The cage 1 can also be a cuboid, a triangular column, a hexagonal column or a cylinder. In this embodiment, the cage 1 has five transparent sides. The image capturing module 4 captures images from the transparent sides.

With reference to FIG. 1, in this embodiment, the image capturing module 4 comprises a first image capturing element 41 and a second image capturing element 42. The first image capturing element 41 corresponds to the transparent side 101 and captures the image from the transparent side 101. The second image capturing element 42 corresponds to the transparent side 102 and captures the image from the second transparent side 102.

With reference to FIG. 1, in this embodiment, the transparent side 101 is perpendicular to the transparent side 102. The transparent side 102 contacts the platform 3. The platform 3 comprises a stage transparent portion 31. The transparent side 102 corresponds to the stage transparent portion 31. The second image capturing element 42 corresponds to the stage transparent portion 31 and captures the image from the transparent side 102. In one embodiment, the whole housing of the platform 3 can be made of transparent materials, and the stage transparent portion 31 can be in any position on the platform 3.

With reference to FIG. 1, in this embodiment, the cage 1 is rotated on the platform 3. By rotating the cage 1, the first image capturing element 41 captures four images from the four transparent sides of the cage 1. The second image capturing element 42 corresponds to the stage transparent portion 31 and captures the image from the transparent side 102. Therefore, the image capturing module 4 captures five images of the object T.

Figure 3:
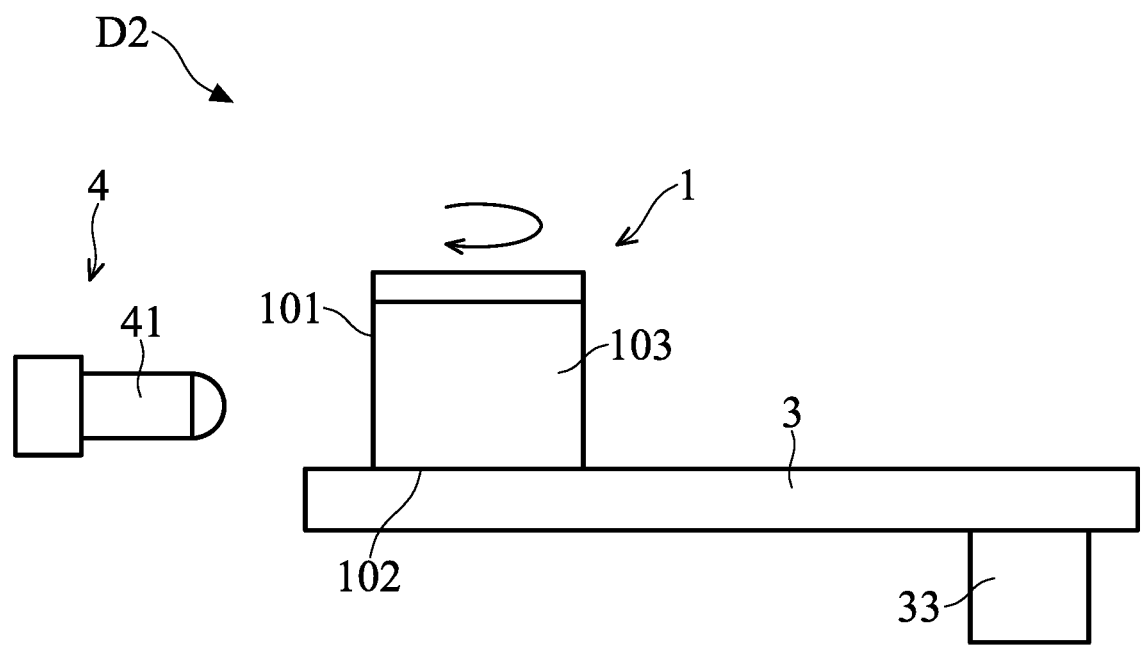
FIG. 3 shows an inspection device of another embodiment of the invention.

FIG. 3 shows an inspection device D2 of another embodiment of the invention. With reference to FIG. 3, in this embodiment, the image capturing module 4 comprises only the first image capturing element 41. The cage 1 is rotated relative to the first image capturing element 41. The first image capturing element 41 captures the images from the transparent side 101 and the transparent side 103 (or, further captures the images from the transparent side 104 and the transparent side 105). In this embodiment, by rotating the cage 1, the first image capturing element 41 captures four images of the object T from the four transparent sides of the cage 1.

In the embodiment above, the cage 1 is rotated on the platform 3 to be rotated relative to the first image capturing element 41. However, the disclosure is not meant to restrict the invention. In another embodiment, the cage 1 can be rested on the platform 3, and the first image capturing element 41 is rotated around the cage 1. Therefore, the cage 1 is also rotated relative to the first image capturing element 41.

Figure 4A:
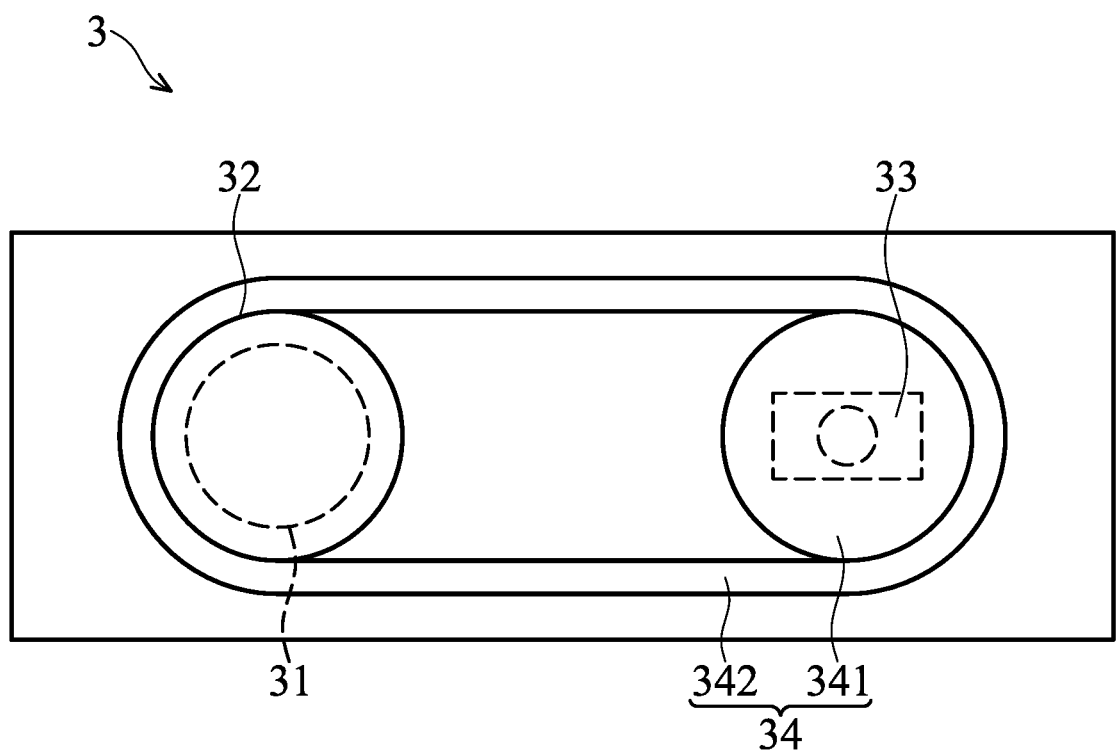
FIG. 4A shows a platform of an embodiment of the invention.

FIG. 4A shows the platform 3 of an embodiment of the invention. With reference to FIG. 4A, in this embodiment, the platform 3 comprises a rotational plate 32, an actuator 33 and a transmission unit 34. The actuator 33 is connected to the transmission unit 34. The transmission unit 34 is connected to the rotational plate 32. The actuator 33 moves the transmission unit 34. The transmission unit 34 rotates the rotational plate 32. The stage transparent portion 31 is formed on the rotational plate 32. In one embodiment, the rotational plate 32 can be partially transparent, totally transparent or hollow. The stage transparent portion 31 is on the transparent portion or the hollow portion of the rotational plate 32.

With reference to FIG. 4A, in this embodiment, the actuator 33 is a motor. The transmission unit 34 comprises a pulley 341 and a belt 342. The pulley 341 is connected to the motor, and the belt 342 connects the pulley 341 to the rotational plate 32.

Figure 4B:
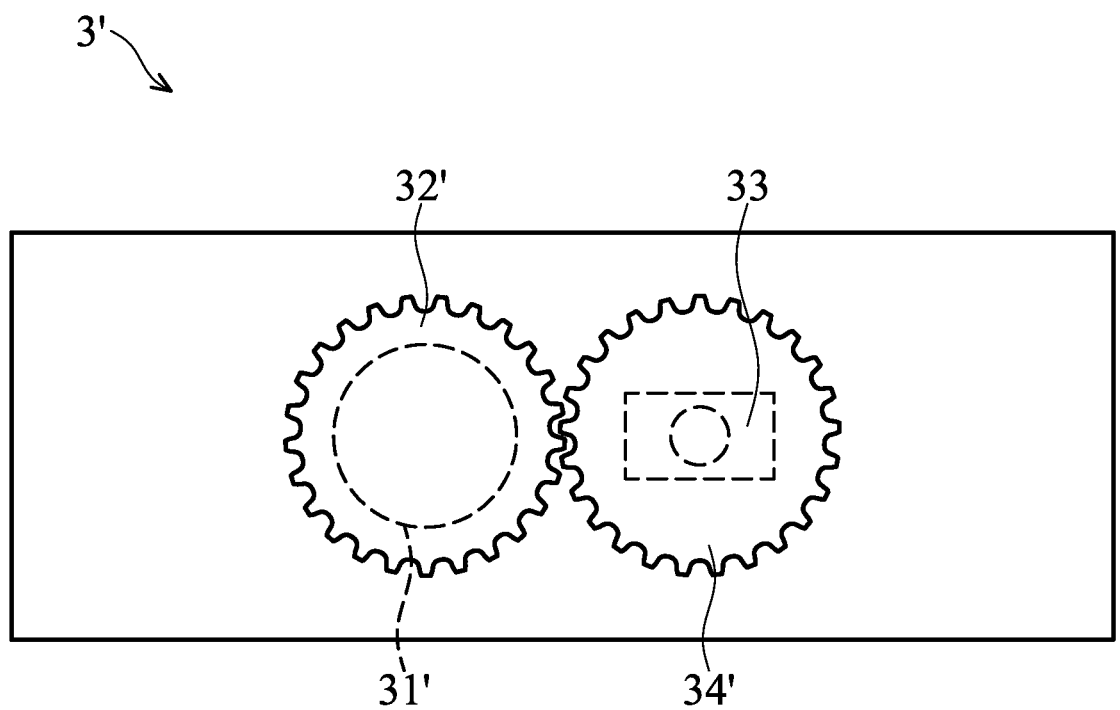
FIG. 4B shows a platform of another embodiment of the invention.

FIG. 4B shows the platform 3' of another embodiment of the invention. With reference to FIG. 4B, in this embodiment, the actuator 33 is a motor. The transmission unit 34' comprises a gear. The gear is connected to the motor. The gear rotates the rotational plate 32'. The stage transparent portion 31' is formed on the rotational plate 32'. In this embodiment, the rotational plate 32' (gear) can be totally transparent or partially transparent, or hollow. The stage transparent portion 31' is on the transparent portion or the hollow portion of the rotational plate 32' (gear).

Figure 5:
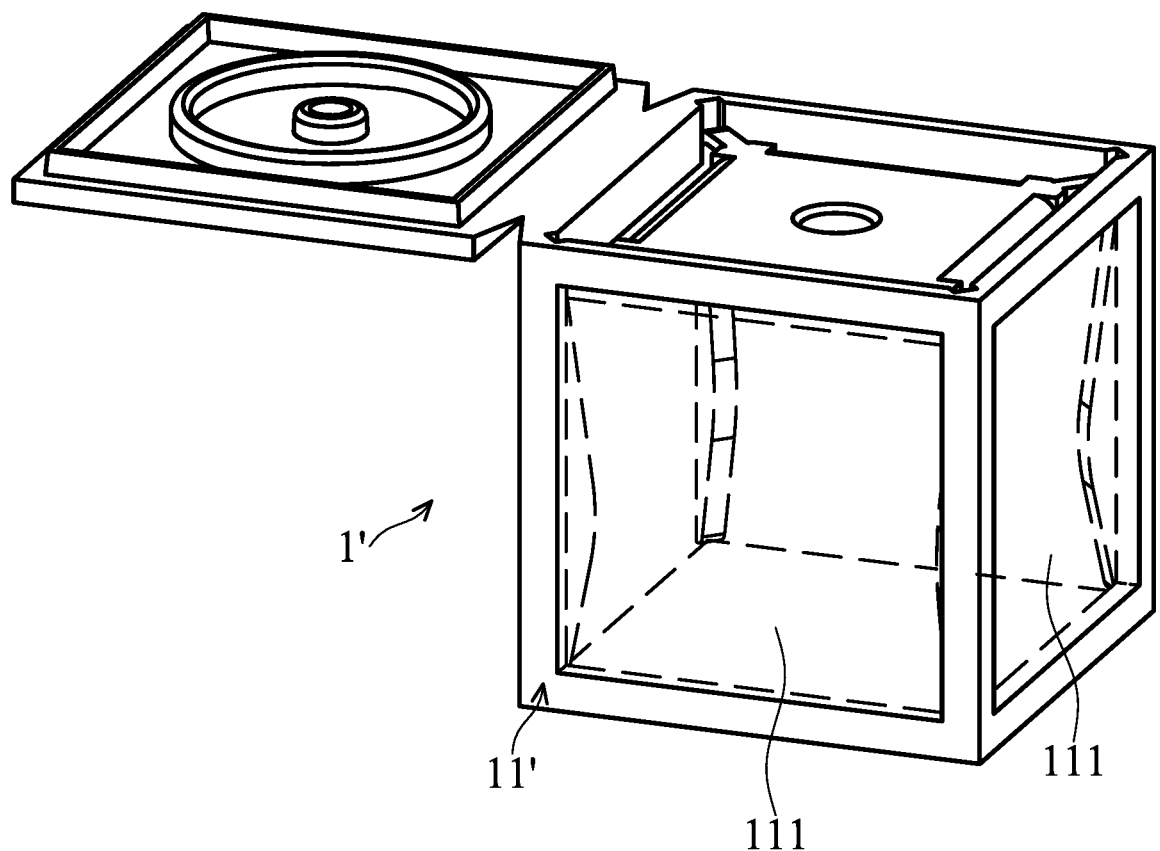
FIG. 5 shows a cage of another embodiment of the invention.

FIG. 5 shows a cage 1' of another embodiment of the invention. With reference to FIG. 5, in this embodiment, the cage body 11' comprises a plurality of transparent plates 111. The transparent plates 111 are embedded to surfaces of the cage body 11'. The transparent sides mentioned above are formed on the transparent plates 111. In this embodiment, the cage body 11' (for example, the cube frame) can be made of an opaque material. The transparent plates 111 can be made of glass or another transparent material.

Figure 2C:
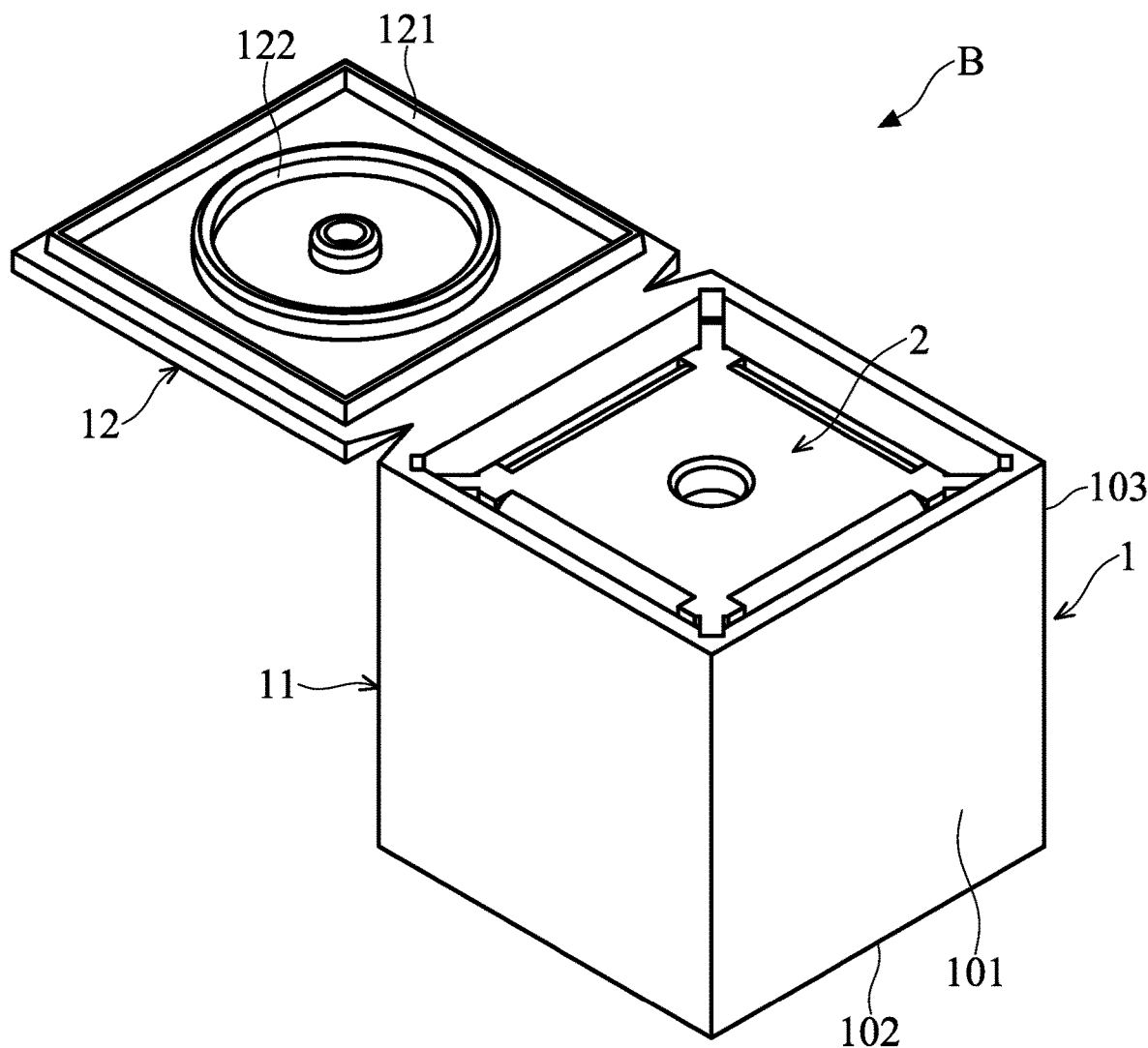
FIG. 2C is an assembled view of the inspection cage unit of the embodiment of the invention.
Figure 2D:
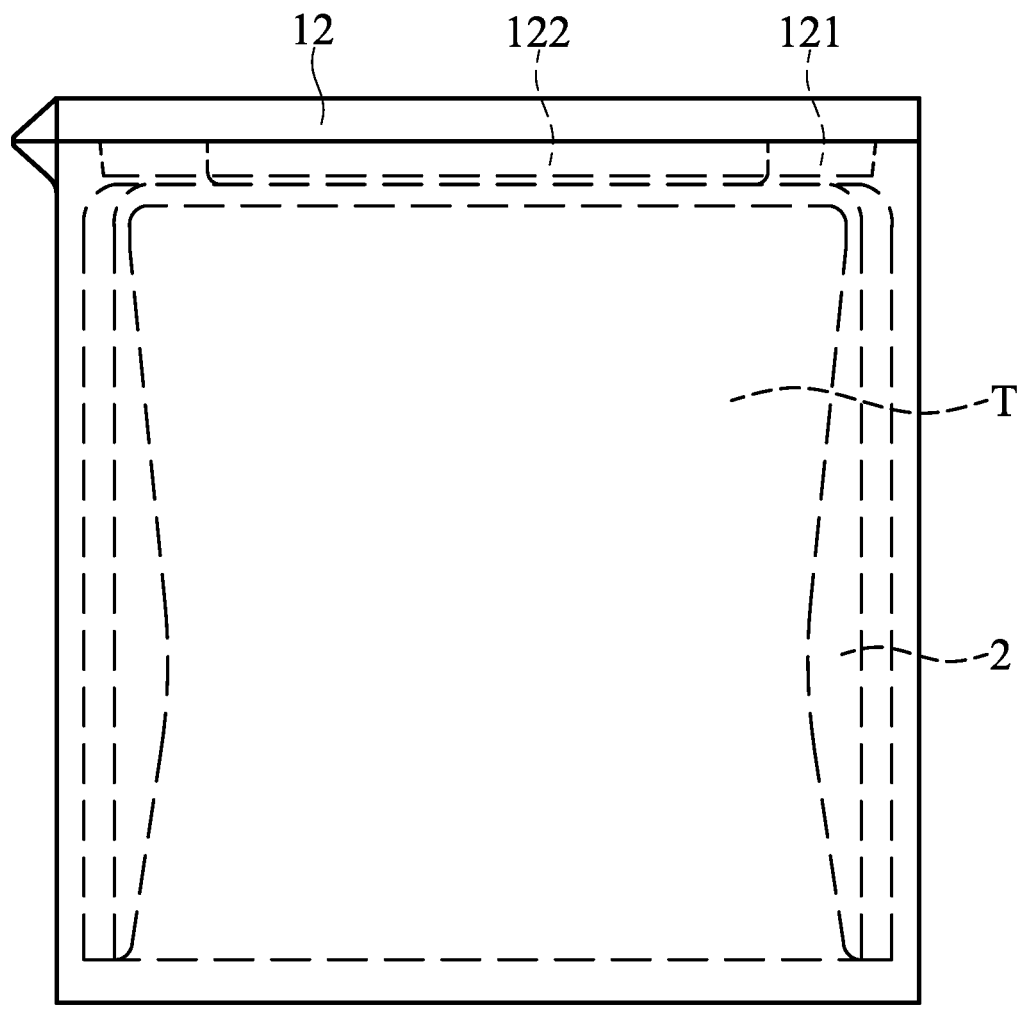
FIG. 2D is a side view of the inspection cage unit of the embodiment of the invention.

With reference to FIGS. 2A, 2C and 2D, in one embodiment, the cage cover 12 comprises an O-ring 121. When the cage cover 12 seals the cage body 11, the O-ring 121 abuts an inner wall of the cage body 11. In one embodiment, the cage cover 12 comprises an abutting portion 122. When the cage cover 12 seals the cage body 11, the abutting portion 122 abuts the holder 2.

Figure 6:
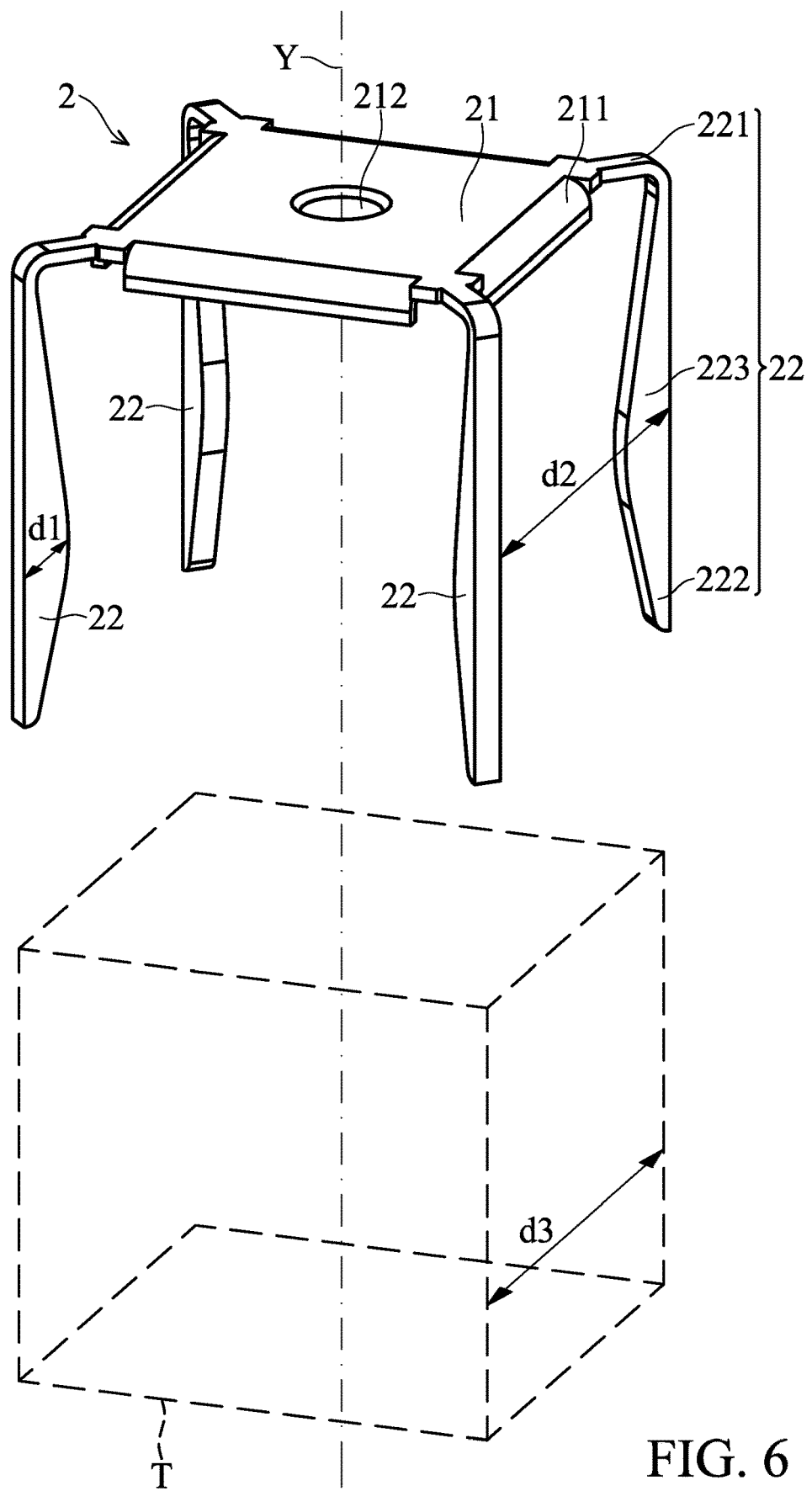
FIG. 6 shows the details of a holder of an embodiment of the invention.

With reference to FIG. 6, in one embodiment, the holder 2 comprises a base 21 and a plurality of cantilever arms 22. The cantilever arms 22 are connected to the base 21. In one embodiment, the cantilever arms 22 may be inserted into the object T. The base 21 abuts the object T. When the cage cover 12 seals the cage body 11, the cage cover 12 abuts the base 21.

With reference to FIG. 6, in one embodiment, each cantilever arm 22 comprises a first end 221, a second end 222 and a pressing portion 223. The pressing portion 223 is located between the first end 221 and the second end 222. The first end 221 is connected to the base 21, and the second end 222 is a free end. In one embodiment, each pressing portion 223 is sheet-shaped, and a width d1 of the pressing portion 223 is greater than widths of other portions of the cantilever arm 22. In this embodiment, the pressing portion 223 extends toward a central axis Y of the holder 2.

In the embodiment above, the pressing portion 223 is located between the first end 221 and the second end 222. For example, the pressing portion 223 is located in the middle of the first end 221 and the second end 222, and presses the central portion of the object T. The central portion of the object T is therefore sufficiently attached to the lateral transparent sides.

With reference to FIG. 6, in one embodiment, the distance d2 between the cantilever arms 22 is slightly smaller than the width d3 of the object T. Therefore, the cantilever arms 22 can be sufficiently inserted into the object T. In this embodiment, the cantilever arms 22 are parallel to each other. In one embodiment, when the holder 2 is out of the cage 1, the free ends (the second ends 222) of the cantilever arms 22 slightly deviate from the central axis Y. With reference to FIGS. 2A and 6, the cage body 11 comprises a plurality of corners 112. When the holder 2 and the object T are desired to be received in the cage 1, the object T and the cantilever arms 22 are pressed into the cage 1, and the cantilever arms 22 respectively abut the corners 112 by elastic force.

With reference to FIG. 6, in one embodiment, the base 21 comprises at least one bending portion 211, and the bending portion 211 is located between the two adjacent cantilever arms 22. The bending portion 211 press the object T, and the bottom of the object T is therefore sufficiently attached to the bottom transparent side.

Figure 7:
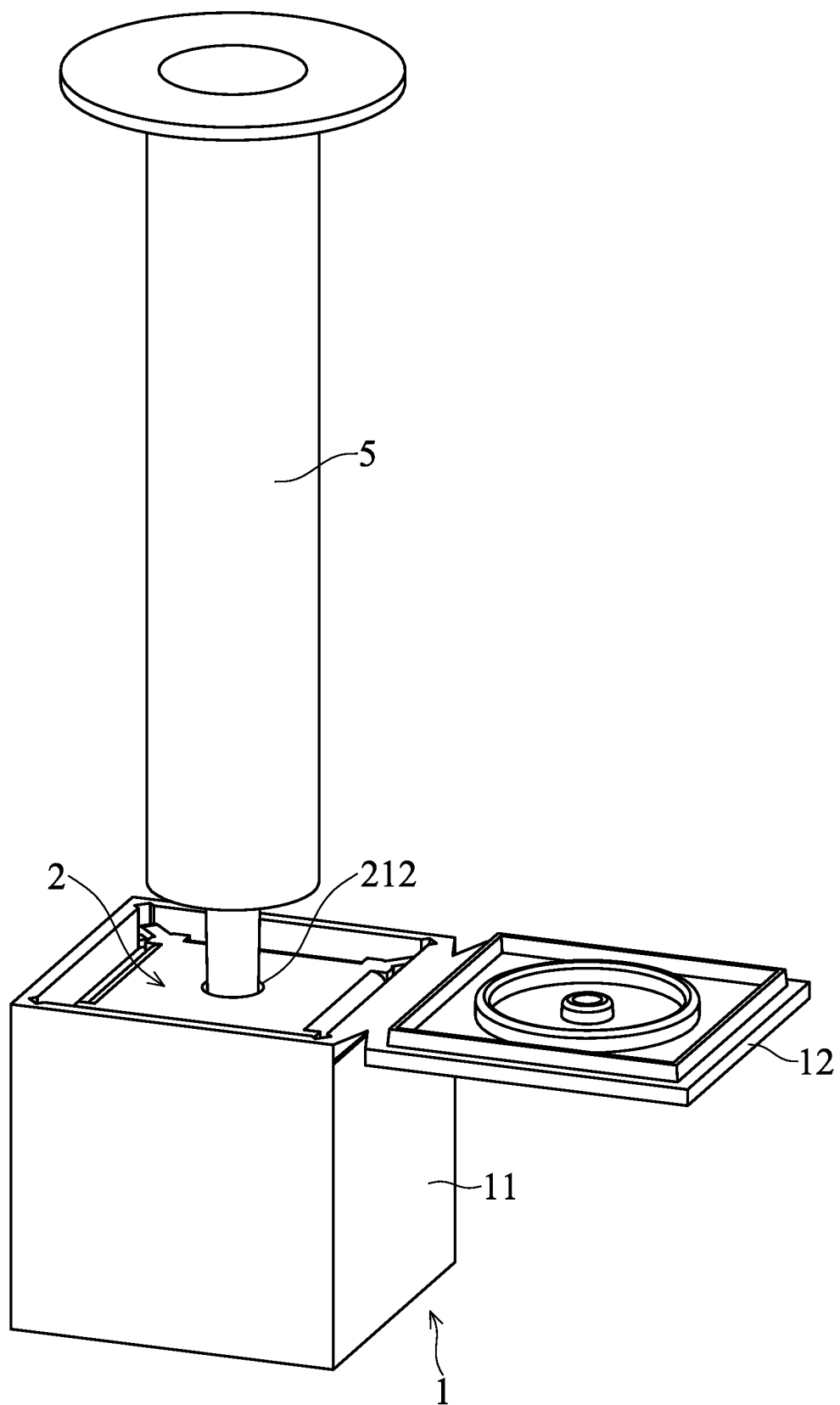
FIG. 7 shows an injector and an embodiment of the invention.

With reference to FIG. 7, in one embodiment, the inspection device further comprises an injector 5. The base 21 further comprises a wedging hole 212. The injector 5 is adapted to be connected to the wedging hole 212. After the holder 2 and the object T are placed into the cage body 11, glycerin can be injected into the cage body 11 by the injector 5. By soaking the object T (biological tissue) in the glycerin, the object T (biological tissue) is moisturized and the image of the object T (biological tissue) is clarified. The glycerin can be replaced by other liquid with similar function. After the glycerin is injected into the cage body 11, the cage cover 12 covers the cage body 11, and the cage 1 is placed on the platform to be inspected.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An inspection device, comprising:
    a platform;
    a cage, disposed on the platform, wherein the cage comprises a first transparent side and a second transparent side, and the first transparent side and the second transparent side are not coplanar;
    a holder, disposed in the cage; and
    an image capturing module, capturing a first image from the first transparent side, or capturing a second image from the second transparent side,
    wherein the platform comprises a rotational plate, an actuator and a transmission unit, the actuator is connected to the transmission unit, the transmission unit is connected to the rotational plate, the actuator moves the transmission unit, and the transmission unit rotates the rotational plate.

2. The inspection device as claimed in claim 1, wherein the image capturing module comprises a first image capturing element and a second image capturing element, the first image capturing element corresponds to the first transparent side and captures the first image from the first transparent side, and the second image capturing element corresponds to the second transparent side and captures the second image from the second transparent side.

3. The inspection device as claimed in claim 2, wherein the first transparent side is perpendicular to the second transparent side, the second transparent side contacts the platform, the platform comprises a stage transparent portion, the second transparent side corresponds to the stage transparent portion, the second image capturing element corresponds to the stage transparent portion and captures the second image from the second transparent side.

4. The inspection device as claimed in claim 1, wherein the image capturing module comprises a first image capturing element, the cage is rotated relative to the first image capturing element, the first image capturing element captures the first image from the first transparent side, and captures the second image from the second transparent side.

5. The inspection device as claimed in claim 4, wherein the stage transparent portion is formed on the rotational plate.

6. The inspection device as claimed in claim 5, wherein the actuator comprises a motor, the transmission unit comprises a pulley and a belt, the pulley is connected to the motor, and the belt connects the pulley to the rotational plate.

7. The inspection device as claimed in claim 5, wherein the actuator comprises a motor, the transmission unit comprises a gear, the gear is connected to the motor, the gear rotates the rotational plate, and the stage transparent portion is formed on the rotational plate.

8. The inspection device as claimed in claim 1, wherein the cage comprises a cage body and a cage cover, the cage body comprises the first transparent side and the second transparent side, the holder is disposed in the cage body, the cage cover covers the holder and seals the cage body, the cage body is made of a transparent material, the holder comprises a base and a plurality of cantilever arms, the cantilever arms are connected to the base, when the cage cover seals the cage body, the cage cover abuts the base, each cantilever arm comprises a first end, a second end and a pressing portion, the pressing portion is located between the first end and the second end, the first end is connected to the base, and the second end is a free end.

9. An inspection cage unit, comprising:
a cage, comprising a first transparent side and a second transparent side, wherein the first transparent side and the second transparent side are not coplanar; and
a holder, disposed in the cage,
wherein the cage comprises a cage body and a cage cover, the cage body comprises the first transparent side and the second transparent side, the holder is disposed in the cage body, the cage cover covers the holder and seals the cage body,
wherein the holder comprises a base and a plurality of cantilever arms, the cantilever arms are connected to the base, and when the cage cover seals the cage body, the cage cover abuts the base.

10. The inspection cage unit as claimed in claim 9, wherein the whole cage body is made of a transparent material.

11. The inspection cage unit as claimed in claim 9, wherein the cage body comprises a first transparent plate and a second transparent plate, the first transparent plate and the second transparent plate are embedded to the cage body, the first transparent side is formed on the first transparent plate, the second transparent side is formed on the second transparent plate.

12. The inspection cage unit as claimed in claim 9, wherein the cage cover comprises an O-ring, and when the cage cover seals the cage body, the O-ring abuts an inner wall of the cage body.

13. The inspection cage unit as claimed in claim 9, wherein the cage cover comprises an abutting portion, and when the cage cover seals the cage body, the abutting portion abuts the holder.

14. The inspection cage unit as claimed in claim 9, wherein each cantilever arm comprises a first end, a second end and a pressing portion, the pressing portion is located between the first end and the second end, the first end is connected to the base, and the second end is a free end.

15. The inspection cage unit as claimed in claim 14, wherein each pressing portion is sheet-shaped, and a width of the pressing portion is greater than widths of other portions of the cantilever arm.

16. The inspection cage unit as claimed in claim 9, wherein the cage body comprises a plurality of corners, and when the holder is in the cage body, the cantilever arms respectively abut the corners.

17. The inspection cage unit as claimed in claim 9, wherein the base comprises at least one bending portion, and the bending portion is located between the two adjacent cantilever arms.

18. The inspection cage unit as claimed in claim 9, wherein the cage body is made of a transparent material, the holder comprises a base and a plurality of cantilever arms, the cantilever arms are connected to the base, when the cage cover seals the cage body, the cage cover abuts the base, each cantilever arm comprises a first end, a second end and a pressing portion, the pressing portion is located between the first end and the second end, the first end is connected to the base, and the second end is a free end.

* * * * *